United States Patent [19]
Battiato et al.

[11] Patent Number: 5,855,568
[45] Date of Patent: Jan. 5, 1999

[54] ANGIOGRAPHIC SYRINGE AND LUER CONNECTOR

[75] Inventors: Dane J. Battiato, Cincinnati, Ohio; Gary S. Wagner, Taylor Mill, Ky.; Steve P. Verdino, Cincinnati; Robert G. Bergen, Westchester, both of Ohio; James E. Knipfer, Ft. Wright, Ky.; Pamela K. Jacobs, Loveland; James H. Goethel, Cincinnati, both of Ohio

[73] Assignee: Liebel-Flarsheim Company, Cincinnati, Ohio

[21] Appl. No.: 753,283

[22] Filed: Nov. 22, 1996

[51] Int. Cl.$^6$ .................................................. A61M 5/00
[52] U.S. Cl. .............................. 604/240; 604/241
[58] Field of Search ....................... 604/239, 240, 604/241–243, 283, 905, 174; 128/912; 285/38, 92, 340, 360

[56] References Cited

U.S. PATENT DOCUMENTS

| | | |
|---|---|---|
| Re. 31,873 | 4/1985 | Howes . |
| 1,683,349 | 9/1928 | Hein . |
| 1,740,459 | 12/1929 | Hein . |
| 1,842,352 | 1/1932 | Krueger .............................. 604/241 X |
| 2,347,469 | 4/1944 | Dies . |
| 2,443,394 | 6/1948 | LeClaire . |
| 2,454,557 | 11/1948 | Jacobson . |
| 2,511,396 | 6/1950 | Brekke . |
| 2,772,898 | 12/1956 | Seeler . |
| 2,855,927 | 10/1958 | Henderson . |
| 2,893,395 | 7/1959 | Buck . |
| 2,988,385 | 6/1961 | Foelster et al. . |
| 3,127,892 | 4/1964 | Bellamy, Jr. et al. . |
| 3,301,256 | 1/1967 | Cowley . |
| 3,372,697 | 3/1968 | Keller . |
| 3,394,954 | 7/1968 | Sarns . |
| 3,402,713 | 9/1968 | Senkowski et al. . |
| 3,469,581 | 9/1969 | Burke . |
| 3,507,279 | 4/1970 | Senkowski . |

(List continued on next page.)

FOREIGN PATENT DOCUMENTS

| | | |
|---|---|---|
| 1552417 | 1/1969 | France . |
| 2075870 | 10/1971 | France . |
| 2127866 | 10/1972 | France . |
| 2369471 | 5/1978 | France . |
| 1204896 | 11/1965 | Germany . |
| 1750187 | 11/1975 | Germany . |
| 3223462 | 6/1982 | Germany . |
| 617654 | 7/1978 | U.S.S.R. . |
| 1192579 | 5/1970 | United Kingdom . |
| 1192580 | 5/1970 | United Kingdom . |
| 1397493 | 6/1975 | United Kingdom . |
| 2077379 | 12/1981 | United Kingdom . |
| 2122707 | 1/1984 | United Kingdom . |

OTHER PUBLICATIONS

Barber Colman, *Viamonte/Hobbs Injector Model 2000 Instruction Manual,* Barber–Colman Company Instruction Manual 1970.

Barber Colman, *The Disposables,* Barber–Colman Company Sales Brochures 1972.

Barber Colman, *Viamonte/Hobbs Injector Model 2000,* Barber–Colman Company Sales Brochure 1972.

*Primary Examiner*—Ronald Stright, Jr.
*Assistant Examiner*—A. T. Nguyen
*Attorney, Agent, or Firm*—Wood, Herron & Evans, L.L.P.

[57] ABSTRACT

A syringe discharge end having a rotatable tubular connector member for engaging a luer connector on medical tubing. The syringe discharge end and the connector have mating threads which are used to affix the connector to the syringe discharge end. Once affixed, the connector is may freely rotate relative to the syringe, while being prevented from axial movement. On its distal end, the connector includes internal threads for engaging external threads on a standard luer connector of medical tubing. To engage the connector to tubing, the connector is rotated relative to the tubing and the syringe to draw the tubing onto the syringe discharge end.

6 Claims, 3 Drawing Sheets

U.S. PATENT DOCUMENTS

| | | |
|---|---|---|
| 3,514,131 | 5/1970 | McKinney . |
| 3,542,024 | 11/1970 | Burke . |
| 3,594,022 | 7/1971 | Woodson . |
| 3,601,151 | 8/1971 | Winnard . |
| 3,684,321 | 8/1972 | Hundhausen et al. . |
| 3,752,145 | 8/1973 | Runnells et al. . |
| 3,752,510 | 8/1973 | Windischman et al. . |
| 3,785,683 | 1/1974 | Adelhed . |
| 3,876,234 | 4/1975 | Harms . |
| 3,890,970 | 6/1975 | Gullen . |
| 3,984,133 | 10/1976 | Bird . |
| 4,027,669 | 6/1977 | Johnston et al. . |
| 4,046,479 | 9/1977 | Paley . |
| 4,076,285 | 2/1978 | Martinez .............................. 604/242 X |
| 4,098,276 | 7/1978 | Bloom et al. . |
| 4,123,091 | 10/1978 | Cosentino et al. . |
| 4,133,312 | 1/1979 | Burd . |
| 4,187,848 | 2/1980 | Taylor . |
| 4,191,185 | 3/1980 | Lemieux . |
| 4,210,173 | 7/1980 | Choksi et al. . |
| 4,212,335 | 7/1980 | Bova . |
| 4,240,422 | 12/1980 | Hazen . |
| 4,240,428 | 12/1980 | Akhavi . |
| 4,246,932 | 1/1981 | Raines . |
| 4,254,773 | 3/1981 | Waldbillig . |
| 4,266,815 | 5/1981 | Cross . |
| 4,288,112 | 9/1981 | Stoll . |
| 4,294,250 | 10/1981 | Dennehey . |
| 4,296,949 | 10/1981 | Muetterties et al. . |
| 4,313,440 | 2/1982 | Ashley . |
| 4,323,065 | 4/1982 | Kling . |
| 4,340,148 | 7/1982 | Beckham . |
| 4,346,703 | 8/1982 | Dennehey et al. . |
| 4,369,781 | 1/1983 | Gilson et al. . |
| 4,416,273 | 11/1983 | Grimes . |
| 4,432,764 | 2/1984 | Lopez . |
| 4,433,862 | 2/1984 | Raulins et al. . |
| 4,452,473 | 6/1984 | Ruschke . |
| 4,469,827 | 9/1984 | Pusineri et al. . |
| 4,490,142 | 12/1984 | Silvern . |
| 4,504,268 | 3/1985 | Herlitze . |
| 4,535,820 | 8/1985 | Raines . |
| 4,573,978 | 3/1986 | Reilly . |
| 4,607,868 | 8/1986 | Harvey et al. . |
| 4,623,343 | 11/1986 | Thompson . |
| 4,628,969 | 12/1986 | Jurgens, Jr. et al. . |
| 4,629,455 | 12/1986 | Kanno . |
| 4,636,198 | 1/1987 | Stade . |
| 4,639,019 | 1/1987 | Mittleman . |
| 4,668,217 | 5/1987 | Isono . |
| 4,677,980 | 7/1987 | Reilly et al. . |
| 4,685,910 | 8/1987 | Schweizer . |
| 4,705,509 | 11/1987 | Stade . |
| 4,718,463 | 1/1988 | Jurgens, Jr. et al. . |
| 4,729,401 | 3/1988 | Raines . |
| 4,735,441 | 4/1988 | Stephens . |
| 4,990,140 | 2/1991 | Black . |
| 5,269,762 | 12/1993 | Armbruster et al. . |
| 5,279,569 | 1/1994 | Neer et al. . |

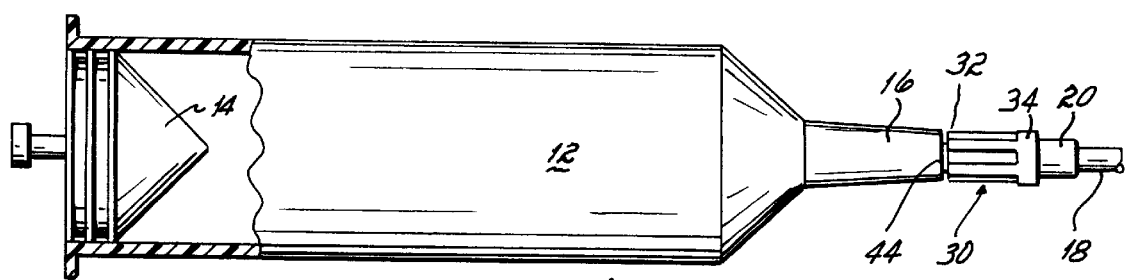
FIG.1
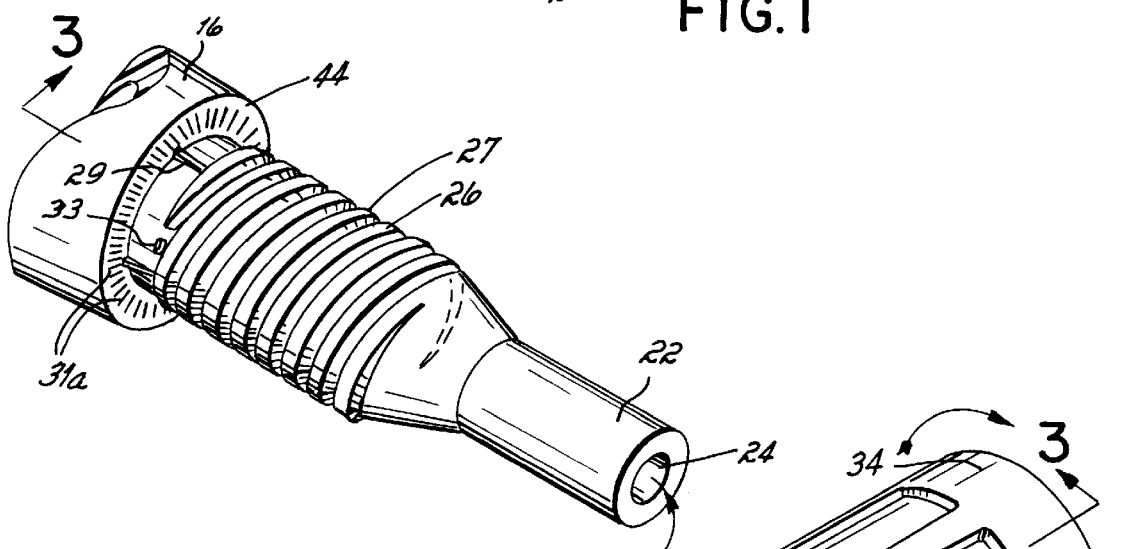
FIG.2
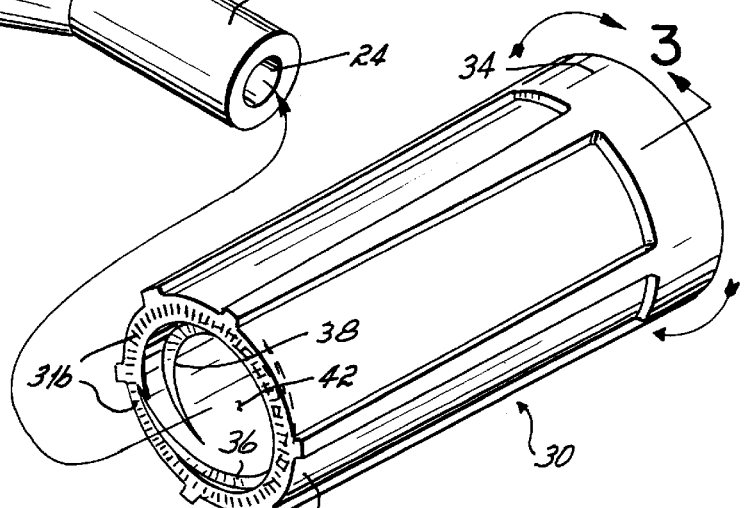
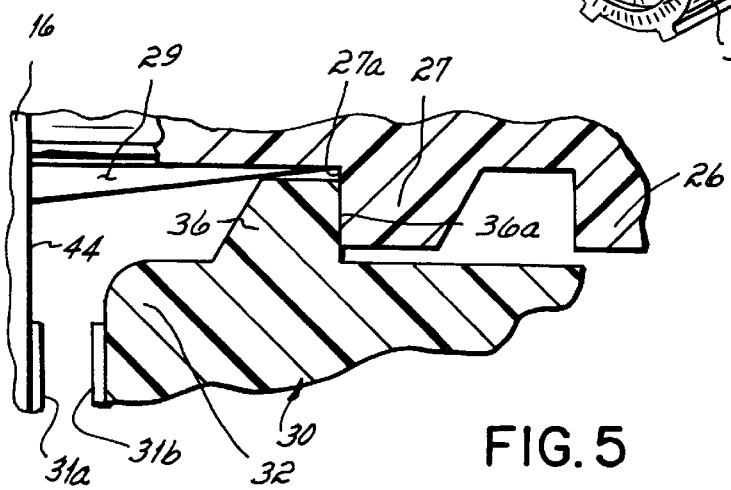
FIG.5

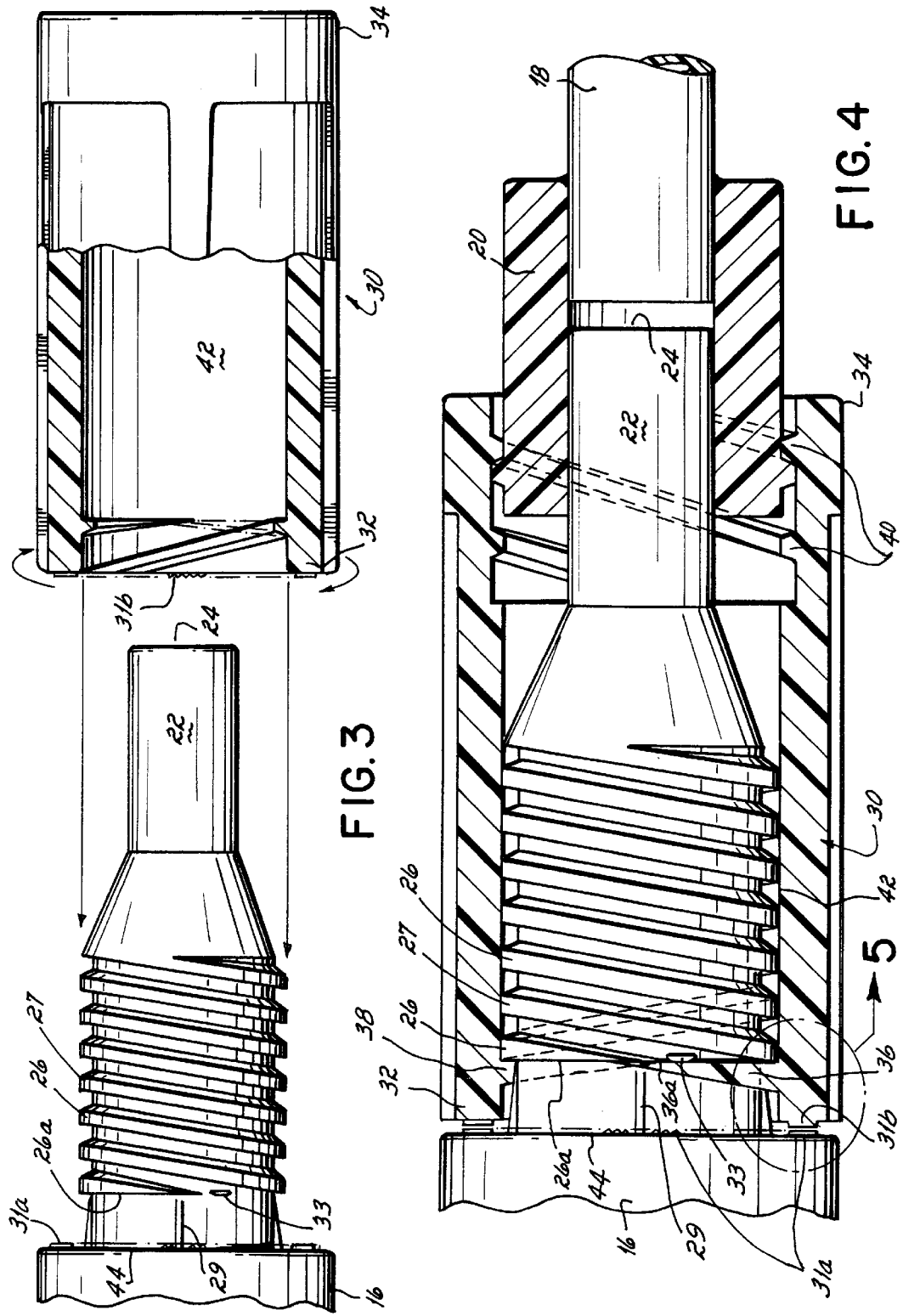

ANGIOGRAPHIC SYRINGE AND LUER CONNECTOR

BACKGROUND OF THE INVENTION

The present invention generally relates to a syringe having a connector for making a connection between the syringe and medical tubing.

Procedures involving the introduction of fluid into a patient's body often require that a syringe be connected through extension tubing to a catheter leading into a patient. One very specific procedure is angiography. Angiography involves introducing radiopaque substances into the blood stream of a patient to facilitate imaging of conditions within the vessels or arteries of the patient, for example, by X-ray equipment. Generally, a catheter is inserted into an appropriate blood vessel for imaging and the other end of the catheter is attached to extension tubing leading to a syringe containing the radiopaque liquid. A connector is required between the extension tubing and the discharge opening of the syringe. This connector should allow connection and disconnection between the end of the syringe and the end of the extension tubing. Not only must the connector facilitate ready connection and disconnection, but it must also be capable of withstanding the high pressures exerted by angiographic injector when the injector is activated to force the radiopaque liquid into the extension tubing and catheter.

Various configurations of syringe discharge ends, connectors and tubing ends have been used to facilitate the connection between the tubing and the syringe. Often, these connections have involved twisting the tubing end onto the syringe discharge end to thereby tighten the connection between respective male and female luer tapers on the syringe discharge end and on the end of the tubing. Another type of connection system is shown, for example, in U.S. Pat. No. 4,573,978 (the '978 patent). This system utilizes an intermediate rotatable connector having internal, oppositely facing tabs at one end and an internally threaded section at the opposite end. The connector also includes intermediate windows or sections void of material. The syringe discharge end includes a tapered section and a circumferential track or recess. The connector is attached to the syringe discharge end by pushing the connector onto the discharge end allowing the tabs to ride up and over the tapered section and then snap into place within the track or recess. The windows allow the connector to have the resilience necessary for the tabs to move away from each other and then snap into the recess. The connector is then held rotatably within the recess and a connection between the syringe discharge end and the tubing end may be made by rotating the connector and threading it onto a suitably formed end of the tubing.

The various connection systems employed in the past for syringes and, more specifically, for angiographic injection systems, each have their own set of disadvantages or problems. Most notably, with respect to the systems requiring that the tubing be twisted relative to the syringe to make the connection, the twisting action to make the connection can be bothersome and inconvenient, since the tubing is often already connected to the patient, and thus it is preferable not to twist the tubing, and in addition, the syringe is typically already locked into an injector apparatus, and thus not rotatable, when the tubing is attached.

The connection system disclosed in the '978 patent has disadvantages associated with the spring locking tabs and windows required in the intermediate connector member. Specifically, the necessary deformation of the connector during the assembly process may weaken the connector and make it more likely to fail. Additionally, the resilience or weakening of the connector may make it more likely to be forced off the syringe discharge end under pressure. Finally, snap fit parts, such as the connector member in the '978 patent, may require manufacturing tolerances which unacceptably increase manufacturing costs.

It would therefore be desirable to provide a connection system for connecting a syringe discharge end to tubing which not only is easy to manufacture, but which is also easy to use by the technical personnel in the field and which is reliable when used uses in high pressure systems, such as angiographic injector systems.

SUMMARY OF THE INVENTION

The present invention serves to alleviate problems in this area by providing a syringe assembly and, more specifically, a unique syringe discharge end and separate connector member. In accordance with the invention, both the syringe discharge end and the connector member have mating threads which not only allow the connector member to be affixed to the discharge end of the syringe, but which ultimately allows free rotational movement of the connector member relative to the syringe while preventing axial movement of the connector member. This unique combination allows the rotatably held connector member to be easily used to connect the syringe tip to a tubing end having, for example, a standard female luer taper. The connector member rotates independently of the tubing and the syringe so that neither the tubing nor the syringe have to be rotated during the connection process. Moreover, both the syringe tip and the connector member may be molded from plastic, for example, in a cost efficient manner. The dual use of threads for both initiating securement of the connector member to the syringe discharge end and providing for a final rotatable connection therebetween provides a connector member which is not only easy to manufacture and assemble but which may also be made as a strong, solid tubular item for withstanding the pressures tending to push the tubing off of the syringe, such as are generated during an angiographic injection processes.

In a conventional manner, the syringe includes a tubular body portion, a distally-located, discharge end portion and a piston disposed for sliding movement within the tubular body portion. In accordance with the invention, the distal discharge end portion includes a narrow tubular extension defining a tip of the discharge end portion and a series of external threads are spaced proximally from the tubular extension on the discharge end portion. A circumferential area that is free of threads is spaced proximally of the external threads on the discharge end portion. The tubular connector member of the present invention includes internal threads at a proximal end and tubing connecting structure at a distal end. The internal threads at the proximal end mate with the external threads of the syringe discharge end and, once the connector member is threaded completely past the external threads of the syringe discharge end, the internal threads are received to freely rotate about the circumferential area which is free of threads on the syringe discharge end.

The internal threads on the connector member comprise a pair of opposed threads each extending between 180° and 360° about an inner wall of the connector member. The preferred type of thread used for both the connector member and the syringe discharge end are double buttress threads.

In specific embodiments, structures are included to ensure that the internal threads of the connector member are not capable of being threaded back toward the tip of the syringe once they are received about the circumferential area which is free of threads. Specifically, protrusions are formed between the external threads of the syringe discharge end, adjacent to the circumferential area which is free of threads. These protrusions and the proximal edges of the threads on the syringe discharge end, generally lie in a plane perpendicular to an axis of rotation between the connector member and the syringe discharge end. When the connector is threaded onto the syringe discharge end, the internal threads on the connector are forced past these projections and into the circumferential area which is free of threads, at which point the connector is free to rotate. Thereafter, the projections prevent the internal threads on the connector from threading back into the external threads on the syringe discharge end.

The preferred tubing connecting structure comprises a set of internal threads disposed at the distal end of the connector member. This second set of internal threads is preferably of the type to connect with a standard externally threaded female luer connector affixed to the end of tubing. Of course, other types of threaded or rotatable connections may be used at this end of the connector member which also take advantage of the ability of the connector member to independently rotate with respect to both the syringe and the tubing.

BRIEF DESCRIPTION OF THE DRAWINGS

FIG. 1 is a side elevational view of a syringe constructed in accordance with this invention;

FIG. 2 is an exploded perspective view of the syringe discharge end and connector member of the invention;

FIG. 3 is an exploded view of the connector member and syringe discharge end with the connector member partially fragmented to show internal threads thereof;

FIG. 4 is a side elevational view with the connector member and tubing connector end in full axial cross-section and showing the connector member secured for free rotation on the discharge end of the syringe;

FIG. 5 is an enlarged cross-sectional view of area 5 of FIG. 4 showing the abutting stop surfaces of the respective internal and external threads on the connector member and syringe discharge end;

DETAILED DESCRIPTION OF THE SPECIFIC EMBODIMENTS

Figure 6:
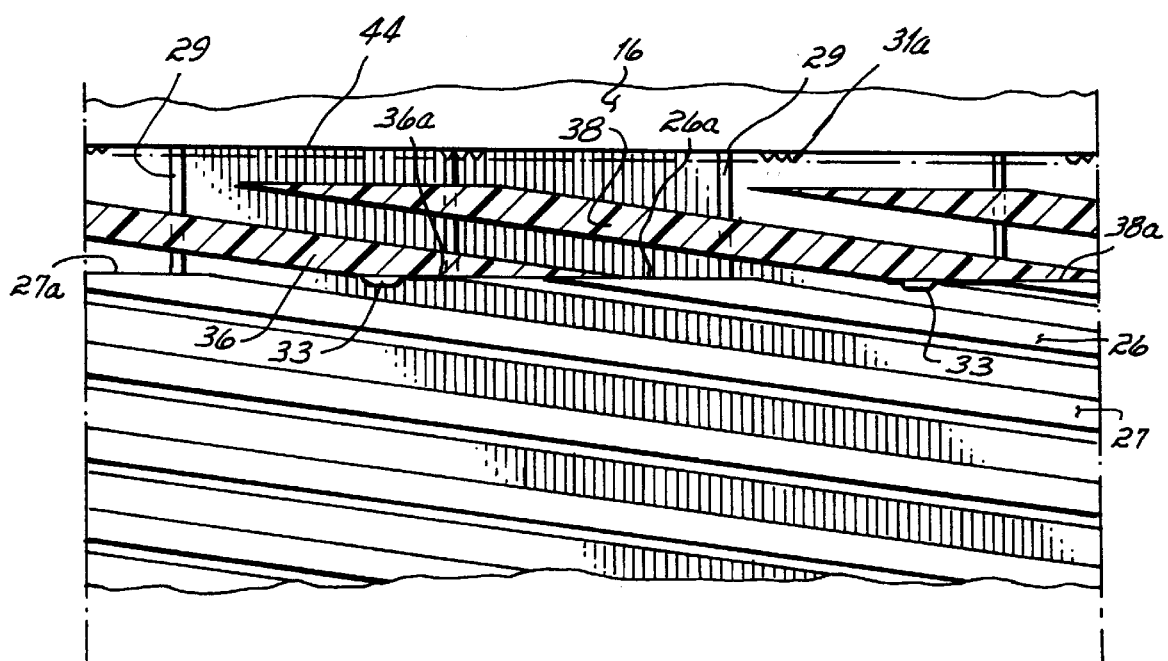
FIG. 6 is a developed view showing the relationship of the connector member threads and the syringe threads when the connector member is secured for free rotation on the syringe.

FIG. 1 illustrates a syringe assembly constructed in accordance with one embodiment of this invention. The syringe assembly includes a syringe 10 having a tubular body portion 12 and a piston 14 which may be conventional in construction. An angiographic injection apparatus (not shown) may be used to move piston 14 back and forth to either draw in or expel radiopaque liquid. Syringe 10 further includes a discharge end 16 which is constructed in accordance with the principles of this invention. Tubing 18 is connected to discharge end 16 using a standard female luer connector 20 affixed to the end of tubing 18. The connection between female luer connector 20 and discharge end 16 is made by a connector 30 according to principles of the present invention as will be discussed further below.

The construction of syringe discharge end 16 and connector 30 is best understood by reference to FIGS. 2–5. Specifically, syringe discharge end 16 includes a narrow tubular extension 22 defining a tip of syringe 10 and having an outlet 24. A series of external threads 26 and 27 is spaced proximally from the tubular extension 22. Threads 26 and 27 are preferably formed as double buttress threads. A circumferential area 28 which is generally smooth and free of threads is disposed proximally of the series of external threads 26 and 27. Within circumferential area 28 are radially extending frictional ribs 29. Planar surface 44, positioned proximally from circumferential area 28, carries radially-extending serrations 31a. Protrusions 33 are positioned between the external threads 26 and 27 on the syringe discharge end 16 adjacent the circumferential area 28 of the syringe, In accordance with principles of the present invention, a tubular connector member 30 is provided for making a connection between tubing 18 (FIG. 1) and syringe discharge end 16. Specifically, as best shown in FIGS. 2–4, tubular connector member 30 includes proximal and distal ends 32 and 34, respectively, each having specific connecting structure. The connecting structure at proximal end 32 comprises a pair of internal threads 36, 38. (Distal end 34 of connector member 30 includes tubing connecting structure which, for example, comprises a series of threads 40 adapted to mate with standard external threads of female luer connector 20—see FIG. 4). Threads 36, 38 are generally opposed to each other and each extends between 180° and 360° about an inner surface 42 of proximal end 32 of connector member 30. The planar surface of proximal end 32 further includes serrations 31b which, in one mode of operation, are matable to serrations 31a on surface 44 of syringe discharge end 16.

Threads 26, 27, 36 and 38 are left-handed double buttress threads. As will be appreciated from a review of FIGS. 3 and 4, threads 36 and 38 thread in a left-handed manner onto threads 26 and 27 of the syringe discharge end 16. Thus, to affix tubular connector member 30 to the syringe discharge end 16, tubular connector member 30 is left-hand threaded onto syringe discharge end 16. As threads 36 and 38 are threaded onto threads 26 and 27, ultimately threads 36 and 38 will come into contact with protrusions 33 formed between threads 26 and 27. Protrusions 33 are sized to produce a slight interference with threads 36 and 38, so that threads 36 and 38 must be forced past protrusion 33 to continue moving tubular connector member 30 onto syringe discharge end 16.

As seen in FIGS. 4 and 6, when tubular connector member 30 is fully connected to the syringe discharge end 16, that is, when threads 36, 38 are rotated completely past the inner ends 26a and 27a of threads 26 and 27, tubular connector member 30 is secured for free rotation relative to syringe discharge end 16 (with a limited frictional resistance produced by ribs 29 to prevent unnecessary spinning of connector 30), but the axial movement of tubular connector member 30 is constrained, because threads 36, 38 are trapped within circumferential area 28 of the syringe discharge end 16. The axial length of threads 36 and 38 on tubular connector 30 is approximately 0.088 inches, whereas the axial length of circumferential area 28 is approximately 0.099 inches. Thus, as seen for example in FIG. 4, there is approximately 0.011 inches of clearance for axial movement of connector 30 after connector 30 is threaded onto the syringe discharge end 16.

Protrusions 33 discourage threads 36 and 38 of the tubular connector member 30 from escaping from the circumferential area 28. Specifically, when tubular connector member 30 is fully threaded on syringe discharge end 16 and threads 36 and 38 are captured within circumferential area 28, as shown in FIGS. 4–6, end portions 36a and 38a of threads 36 and 38, are in opposing face-to-face relation to end portions 26a and 27a of threads 26 and 27, and/or in opposing face-to-face relation to protrusions 33. End portions 36a, 38a, 26a and 27a are generally flattened or formed as shown in FIG. 5, so that their opposing surfaces lie in a plane generally perpendicular to the axis of rotation between connector member 30 and syringe discharge end 16. Accordingly, a large area of contact is formed between end portions 36a, 38a, 26a and 27a, providing support for connector member 30 against pressure tending to push connector member 30 off of discharge end 16 of syringe 10. Furthermore, end portions 36a and 38a of threads 36 and 38 present a planar surface which abuts against protrusions 33 to discourage end portions 36a and 38a from passing into the gap between threads 26 and 27 of the syringe discharge end 16, which thus discourages tubular connector member 30 from threading off of the syringe discharge end 16. Thus, the bearing surfaces of end portions 36a and 38a are adjacent to bearing surfaces 26a and 27a, and/or protrusions 33, during the complete 360° revolution of connector member 30, providing axial support to tubular connector member 30 and discouraging connector member 30 from threading off of the syringe discharge end 16.

It will also be noted that the connecting structure at the distal end 34 of tubular connector member 30 is typically a right-handed threaded connection, i.e., opposite in orientation to the threaded connection between threads 38 and 38 on tubular connector member 30 and threads 26 and 27 of the syringe discharge end 16. As a result, the direction of rotation used to thread tubular connector member 30 onto the discharge end 16 of the syringe, also tightens tubing 18 onto the syringe 10, so that tubular connector member 30 will not thread off of the syringe discharge end 16 while tubing 18 is being tightened onto syringe 10 by rotation of tubular connector member 30.

Thus, in a first mode of operation, tubular connector member 30 is rotated relative to syringe and to tubing end 20 to mate tubing end 20 to tubular extension 22 of syringe 10. In this mode of operation, neither syringe 10 nor tubing 18 need be rotated to achieve a tight connection.

As noted above, proximal end 32 of connector 30 includes serrations 31b which are matable to serrations 31a on surface 44 of syringe discharge end 16. Furthermore, ribs 29 formed in circumferential area 28 are flared outward at their proximal ends, as best seen in FIG. 4. As a result, if proximal end 32 of tubular connector member 30 is pressed against surface 44 of syringe discharge end 16, for example by hand pressure of the operator, tubular connector member 30 will be prevented from rotating as a result of the mating of serrations 31a to serrations 31b, and the increased friction from ribs 29 at their proximal, outwardly flared ends. This permits a second mode of operation, in which tubing can be attached to connector 30 by a one-hand motion; specifically, the tubing is pressed against the distal end 34 of tubular connector member 30, forcing the proximal end 32 of tubular connector member 30 against surface 44 of discharge end 16, and preventing rotary motion. Then, by twisting the tubing connector 20 into the distal end 34 of tubular connector member 30, a connection may be made. This mode of operation may be preferred by users accustomed to connecting tubing to syringe end connectors lacking a rotatable connector, by twisting the tubing connector into the syringe connector.

While the present invention has been illustrated by a description of various embodiments and while these embodiments have been described in considerable detail, it is not the intention of the applicant to restrict or in any way limit the scope of the appended claims to such detail. Additional advantages and modifications will readily appear to those skilled in the art. For example, the connector structure to the tubing might be altered. The syringe connector might be constructed with external threads, connectable to internal threads on the syringe discharge end.

Connector 30 might also be a multi-part unit, having two relatively-rotatable parts, a first part being attachable to the syringe discharge end and a second part attachable to the tubing connector. The invention in its broader aspects is therefore not limited to the specific details, representative apparatus and method, and illustrative example shown and described. Accordingly, departures may be made from such details without departing from the spirit or scope of applicant's general inventive concept.

What is claimed is:

1. A syringe assembly for injecting fluids into the body of an animal through tubing, the assembly comprising:

a syringe having a tubular body portion, a discharge end portion and a piston disposed for sliding movement within said tubular body portion, said discharge end portion having a narrow tubular extension defining a tip of the discharge end portion, a series of external threads spaced proximally from the tubular extension and a circumferential area free of threads spaced proximally of said external threads; and, a tubular connector member having internal threads at a first end and tubing connecting structure at a second end, wherein said internal threads are engageable with the external threads of the syringe discharge end and are configured to be received about said circumferential area when the internal threads are rotated past the external threads of said syringe for allowing free rotation of said tubular connector with respect to the syringe discharge end.

2. The syringe assembly of claim 1 wherein the internal threads of said connector member further comprise a pair of opposed threads each extending between 180° and 360° about an inner wall of said connector member.

3. The syringe assembly of claim 2 wherein the external threads of said syringe and the opposed threads of said connector member have flattened end portions generally lying in a plane perpendicular to an axis of rotation between said connector member and the syringe discharge end, said flattened end portions adapted to generally abut one another when the opposed threads are received within said circumferential area to prevent axial movement of said connector member toward the tip of said discharge end portion.

4. The syringe assembly of claim 2 wherein the external threads on the discharge end portion of said syringe and the pair of opposed threads on said connector member are double buttress threads.

5. The syringe assembly of claim 1 wherein the tubing connecting structure further comprises internal threads.

6. The syringe assembly of claim 1 further comprising a stop surface adjacent to and extending outwardly from said circumferential area, said stop surface limiting axial movement of said connector member when the internal threads of said connector member are received for rotation about said circumferential area.

* * * * *